United States Patent [19]

Wells

[11] Patent Number: 4,597,421

[45] Date of Patent: Jul. 1, 1986

[54] METHOD AND DEVICE FOR ON-COLUMN INJECTION OF A LIQUID SAMPLE INTO SMALL DIAMETER COLUMNS

[75] Inventor: Gregory J. Wells, Suisun, Calif.

[73] Assignee: Varian Associates, Inc., Palo Alto, Calif.

[21] Appl. No.: 672,648

[22] Filed: Nov. 19, 1984

[51] Int. Cl.$^4$ .............................. B65B 3/04
[52] U.S. Cl. ........................... 141/5; 141/31; 141/67; 141/258; 73/23.1; 73/61.1 C; 277/3; 277/DIG. 1; 285/95; 285/96
[58] Field of Search ..................... 141/1–12, 141/31, 67, 250–284; 277/3, DIG. 1; 285/95, 96; 73/23.1, 61.1 C

[56] References Cited

U.S. PATENT DOCUMENTS 4,278,360  7/1981  Lorscheid et al. ............ 141/31

*Primary Examiner*—Houston S. Bell, Jr.
*Attorney, Agent, or Firm*—Stanley Z. Cole; Keiichi Nishimura; David Schnapf

[57] ABSTRACT

A liquid sample in a syringe can be injected into a capillary column with inner diameter less than 200 microns without inserting the injection needle of the syringe into the column. The end of a modified injection needle according to this invention has a tubular opening with inner diameter sufficiently large so that the intake end of the column can be inserted inside, thereby establishing an annular duct between the needle and the column. A carrier gas is caused to flow through this duct while the plunger on the syringe is pressed to squeeze the liquid into the needle, thus forcing the liquid into the capillary column.

13 Claims, 6 Drawing Figures

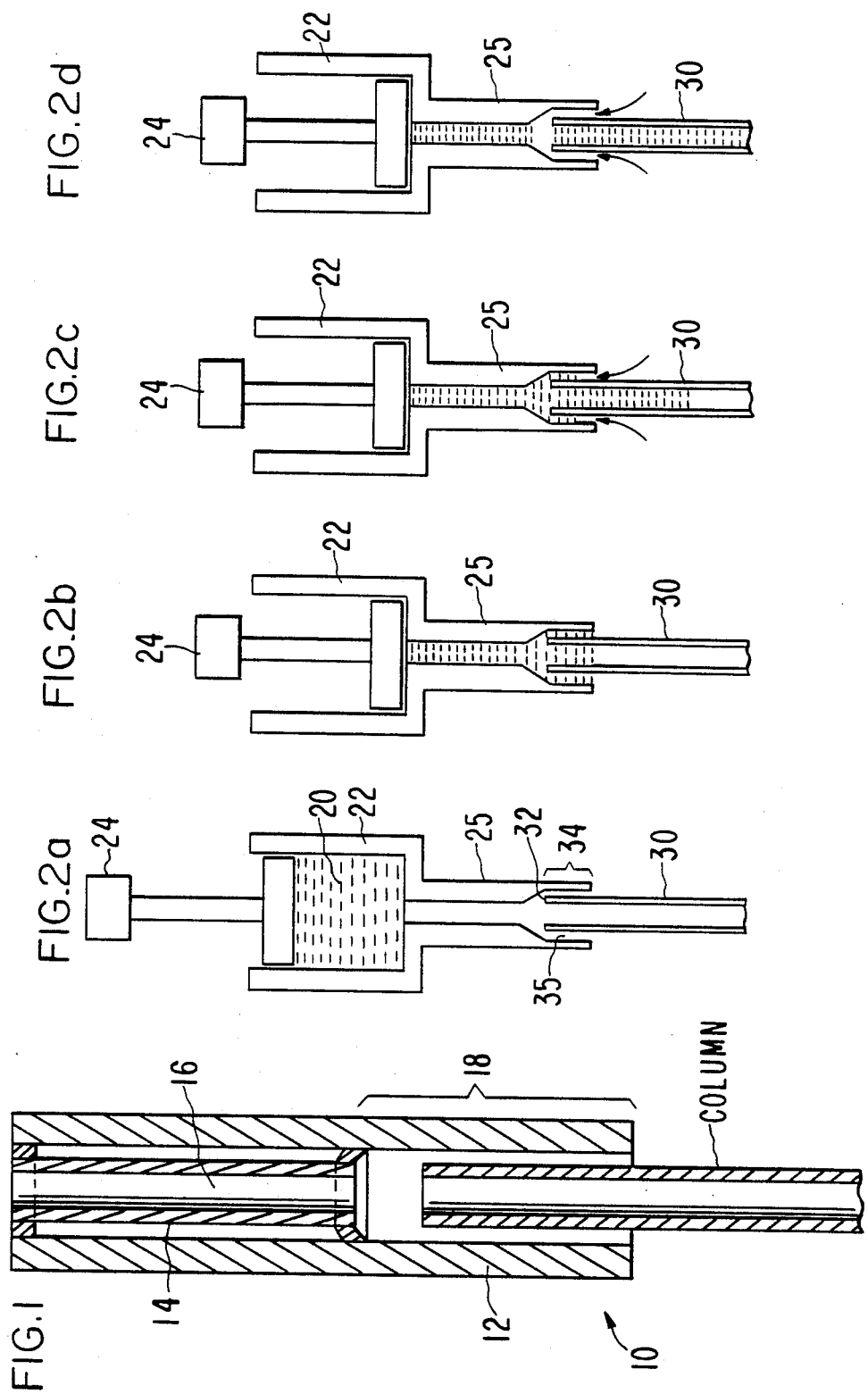

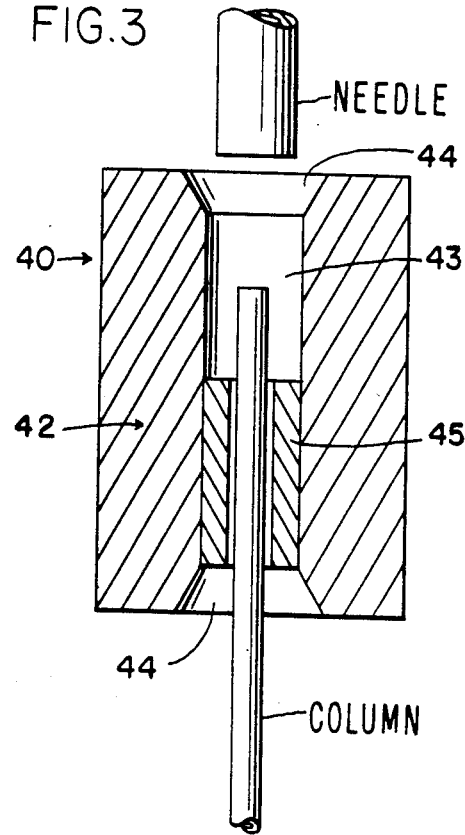

METHOD AND DEVICE FOR ON-COLUMN INJECTION OF A LIQUID SAMPLE INTO SMALL DIAMETER COLUMNS

IN THE BACKGROUND

This invention relates generally to a method and device for introducing a liquid sample into a small diameter column and more particularly to a method and device for on-column injection of a liquid sample into a capillary column with inside diameter less than 200 microns.

Columns of increasingly smaller diameters have been used for gas chromatography. The advantages in using small diameter columns for trace analysis have been described, for example, by J. Hinshaw (5th International Capillary Symposium, Riva Del Garda, 1984). Wall-coated open tubular columns with internal diameters of 100 microns are now commercially available. Flame based detectors such as flame ionization detectors and flame photometric detectors generally provide acceptable performance when using these narrow diameter columns. A new design for an electron capture detector compatible with columns with internal diameters of 100 microns has been disclosed recently by G. Wells and R. Simon (High Res. Chrom. & Chrom. Comm. 6 (1983) 427 and 651) while the use of the split-splitless injection techniques and cold on-column injection with such columns was discussed by Onuska (J. of Chromatogr., 289 (1984) 207). Although the advantages of cold sample introduction into the column are well known in terms of mass discrimination and inertness, the conventional method of using a thin needle to place the sample inside a capillary column has the disadvantage of being limited to columns of inside diameters of about 200 microns or greater since the outer diameter of the needle must necessarily be smaller than the inside diameter of the capillary column. The inside diameter of such a thin needle would be too small and hence impractical. Moreover, a needle with outside diameter not much smaller than the inside diameter of the capillary column may easily scratch the inside of the column when placed directly inside.

SUMMARY OF THE INVENTION

It is therefore an object of this invention to provide a method and device for on-column injection of a liquid sample into a capillary column with inside diameter less than 200 microns.

It is another object of this invention to provide a method of sample introduction into a capillary column without the need for connectors or glued joints on the column or for inserting a needle inside the column.

BRIEF DESCRIPTION OF DRAWINGS

FIG. 1 is a schematic sectional view of a needle embodying the present invention.

FIGS. 2(a)–2(d) show schematically a method of on-column injection embodying the present invention.

FIG. 3 is a schematic sectional view of a needle-alignment means which may be used in connection with the needle and method shown above.

DETAILED DESCRIPTION OF THE INVENTION

According to the present invention which relates to the on-column injection of a liquid sample into a capillary column, the liquid sample is initially inside a syringe of a conventional type equipped with a plunger. It is desired, however, to obviate the need of thrusting the syringe needle into the interior of the capillary column. For this reason, a modified type of needle is used with a conventional syringe according to this invention. These is shown in FIG. 1 an axial cross-sectional view of such a needle 10 comprising a sheath 12 of stainless steel with inner and outer diameters about 0.18 mm and 0.64 mm, respectively, and an uncoated fused silica tube 14 of inner and outer diameters 0.10 mm and 0.16 mm, respectively, sealed into the sheath 12. The silica tube 12 extends to the top (proximate end) of the sheath 12 where the needle 10 joins the syringe (not shown) while the silica tube 12 is terminated at the distal end approximately 8 mm from the bottom. In other words, the needle 10 has therethrough a narrower passageway 16 defined by the silica tube 12 and then an exit end section 18 which defines a wider passageway extending a predetermined distance along the length of the needle 10 at the distal end.

Referring next to FIGS. 2(a)–(d), there is schematically shown how to use according to the present invention a conventional syringe with a needle of the type shown in FIG. 1. FIGS. 2(a)–(d) show the method as a series of operations and, for this reason, same parts are assigned same reference numerals throughout. As shown in FIG. 2(a), a liquid sample 20 to be injected is initially inside the syringe 22 of a conventional type equipped with a plunger 24 and a needle 25 of a type described in FIG. 1. The syringe 22 is so positioned with respect to the capillary column 30 that not only will the needle 25 and the column 30 be mutually coaxial but also the inlet 32 of the column 30 is inside the exit end section 34 of the needle 25, forming an annular duct 35 between the outer wall of the capillary column 30 and the inner wall of the needle 25 inside the exit end section 34. In the next step, the plunger 24 is pressed as shown in FIG. 2(b) so as to push the liquid 20 into the needle 25. A portion of the liquid 20, upon reaching the exit end section 34 with larger inner diameter, will move into the column 30, in part aided by the capillary effect, with the remaining portion moving inside the annular duct 35.

In step 3 which is illustrated in FIG. 2(c), a carrier gas such as helium is introduced through the annular duct 35 (shown symbolically by arrows) in order to push back the liquid 20 from flowing down and out of the annular duct 35. The plunger 24 remains pressed in the meantime and this forces the trapped liquid 20 to move back and into the capillary column 30. In practice, step 2 (FIG. 2(b)) and step 3 (FIG. 2(c)) may be started simultaneously. FIG. 2(d) shows how the liquid 20 is injected into the capillary column 30 as desired, although a small portion of the liquid 20 is trapped by the pressure of the carrier gas above the exit end section 34. Since the internal cross-sectional area of the needle 25 is very small, this means that only a very small fraction of the liquid initially in the syringe may thus be trapped inside the needle.

For the purpose of proper positioning of the syringe with respect to the capillary column as explained above, it is convenient to use an insert device, or a needle-alignment means as shown, for example, in FIG. 3 in an axial cross-sectional form. According to this embodiment, the insert 40 may be an aluminum piece 42 with a cylindrical hole 43 of inner diameter about 0.7 mm completely penetrating it, making funnel-like conical surfaces 44 at both ends. A stainless steel tube 45 of inner diameter about 0.25 mm is pressed on the inner surface of the hole 43, extending about one-half of entire thickness. For the positioning of the needle prior to the operation of FIGS. 2(a)-(d), the column is positioned from below and the needle is lowered from the above as shown in FIG. 3.

The use of smaller diameter columns provides better resolution in addition to lower detection limits because the column bleed noise is less. A experiment using a 1075 split injector instead of an on-column injector showed that there is no apparent loss in resolution caused by the mode of injection; the lower column bleed noise of these smaller diameter columns allows lower detection limits when detectors of other types are used such as a flame ionization detector.

The invention has been described above in terms of only one embodiment but the disclosure given above is intended to be illustrative and hence to be construed broadly. For example, FIGS. 1 and 3 are intended to be schematic diagrams. Dimensions and materials of various parts of the injection needle and the insert means may be freely varied. Regarding the insert means 40 of FIG. 3, in particular, the disclosed method of forming a hole having two sections with different inner diameters is not to be considered as a limitation. The only requirement regarding the inner diameters of the two sections is that the larger inner diameter must be large enough to admit the needle while the smaller diameter must be large enough for the capillary column to pass through but not for the needle. The scope of this invention is limited only by the following claims.

What is claimed is:

1. A method of injecting a liquid sample from a syringe means into a capillary column of inner diameter less than 200 microns through an open intake end thereof, said method comprising the steps of
    connecting to said syringe means a tubular needle having an open injection end so that a course of liquid flow can be established from inside said syringe means through said tubular needle to said open injection end, the inner diameter of said needle being sufficiently larger than the outer diameter of said capillary tube over at least a predetermined length along said needle from said injection end,
    inserting said capillary column inside said needle by said predetermined distance from said open injection end, thereby establishing inside said needle a passage for gas between the inner surface of said tubular needle and said capillary column,
    causing said sample liquid to flow out of said syringe means into said needle, and
    causing a gas to flow through said passage so as to force said liquid into entering said capillary column and to prevent said liquid from flowing through said passage towards said injection end.

2. The method of claim 1 wherein said syringe means is provided with a plunger for applying pressure on said liquid and wherein said step of causing said liquid to flow is achieved by pressing said plunger.

3. The method of claim 2 wherein said step of causing a gas to flow is effected while said plunger remains pressed.

4. The method of claim 1 wherein said inserting step is achieved by providing a needle-alignment means comprising a solid block with a tubular hole therethrough defining a first opening and a second opening.

5. The method of claim 4 wherein said hole defines a first inner diameter along a section including said first opening and a second inner diameter smaller than said first inner diameter along another section including said second opening.

6. The method of claim 4 wherein said inserting step is achieved further by inserting said column through said second opening and inserting said needle through said first opening.

7. An injection needle with an outlet opening at an end thereof for injecting a liquid through said outlet opening into a capillary column of less than 200 microns in inner diameter, said needle comprising a first section having a first inner diameter and a second section having a second inner diameter, said second inner diameter being larger than both said first inner diameter and the outer diameter of said capillary column.

8. The needle of claim 7 wherein said first and second sections comprise a cylindrical tubular sheath having said second inner diameter and said first section includes an inner tube with said inner tube affixed inside said sheath.

9. The needle of claim 8 wherein said tubular sheath is made of stainless steel and said inner tube is made of fused silica.

10. The needle of claim 7 wherein said second section includes said outlet opening.

11. A needle-alignment means for achieving insertion by a predetermined distance of a capillary column inside a cylindrical tubular injection needle through an injection opening at one end thereof, said needle-alignment means comprising a solid block with a tubular hole penetrating therethrough between a first opening and a second opening and defining a first section between said first opening and a junction point and a second section between said section opening and said junction point, said first section of said hole being wide enough for said needle to pass through and said second section of said hole being wide enough for said capillary column to pass through but not for said needle.

12. The needle of claim 7 further comprising means to direct carrier gas under pressure to the space between the outer diameter of the column and the second section of the needle.

13. The needle of claim 7 wherein the capillary column has a diameter of about 100 microns.

* * * * *